April 17, 1962 H. W. LINDHOLM Plant Pat. 2,135

PEACH TREE

Filed Oct. 17, 1960

WITNESS

Addison E. Avery

INVENTOR

Helge W. Lindholm

Webster & Webster

ATTYS.

United States Patent Office

Plant Pat. 2,135
Patented Apr. 17, 1962

2,135
PEACH TREE

Helge W. Lindholm, 2421 10th Ave., Kingsburg, Calif.

Filed Oct. 17, 1960, Ser. No. 63,232
1 Claim. (Cl. 47—62)

This discovery relates to a new and distinct variety of hardy, vigorous, sturdy peach tree which is a regular and very productive bearer of large freestone fruit having yellow flesh streaked with red next to the stone, and yellow skin partially blushed with red.

The present variety of peach tree is characterized, as to novelty:

By a trunk and branches that are more husky and sturdy than the average; the closest resemblance, as to the tree, being to the Rio Oso Gem (United States Plant Patent No. 84).

By a large, freestone, good flavored, fruit which highly colors, remains firm, and hangs well on the tree eight to twelve days before harvest; the flesh also remaining firm from harvest to market and as distinguished from the usual soft flesh of many freestone peaches such as the Elberta (unpatented).

By fruit which colors before the Elberta but harvests later.

By fruit which is comparable in size to the Hale (unpatented), but in shape and firmness of flesh being closer to the Rio Oso Gem.

And by fruit which is of good commercial quality for shipping, canning and freezing; the latter by reason of slow oxidization of the flesh when exposed to atmosphere.

The herein described variety of peach tree was discovered by me growing as a seedling (parentage unknown) in the residence yard of my ranch located near Kingsburg, Fresno County, California. Subsequent to discovery of such seedling, I maintained it under conditions of cultivation and irrigation, and when such seedling grew to maturity, I recognized the distinctive characteristics of it both as to the tree and its fruit.

The variety has been asexually reproduced by me, upon my premises located as aforesaid, by budding as well as grafting; such reproduction, in maturity, having run true to the parent seedling in all respects.

Figure 1:
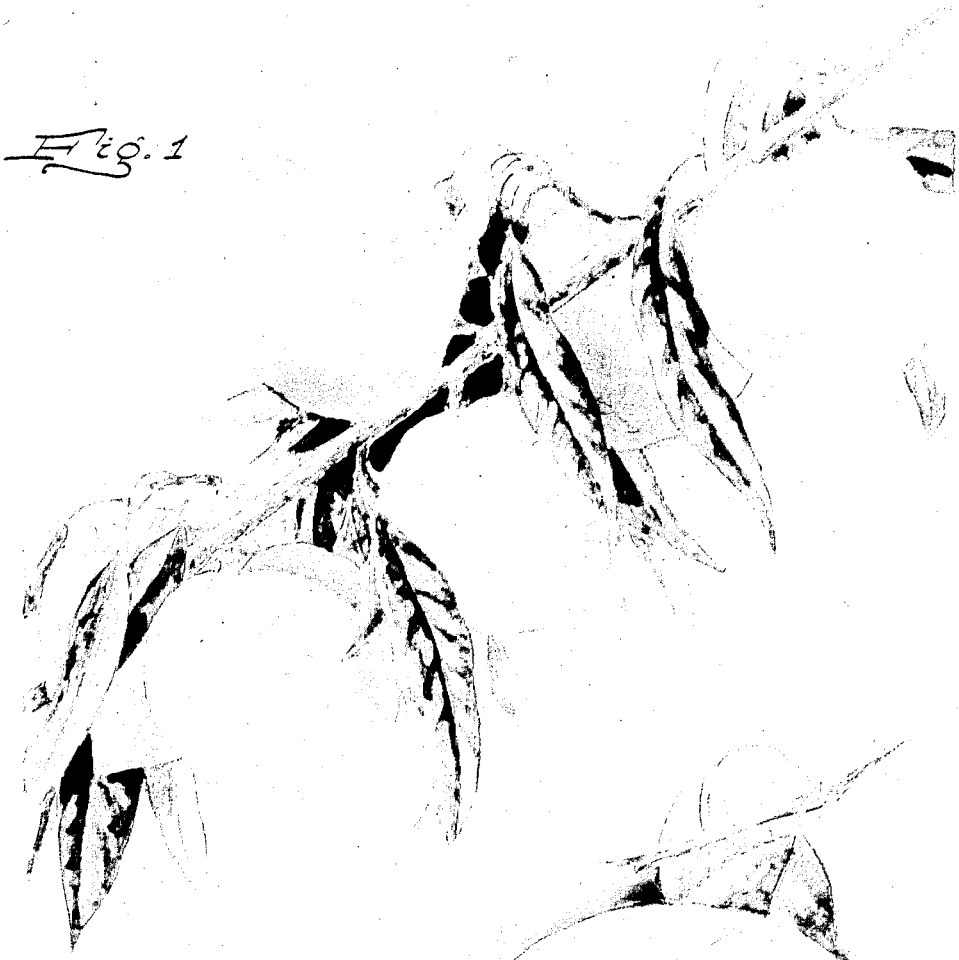
FIG. 1 is an elevation showing a number of the fruit together with bearing twig and leaves.
Figure 2:
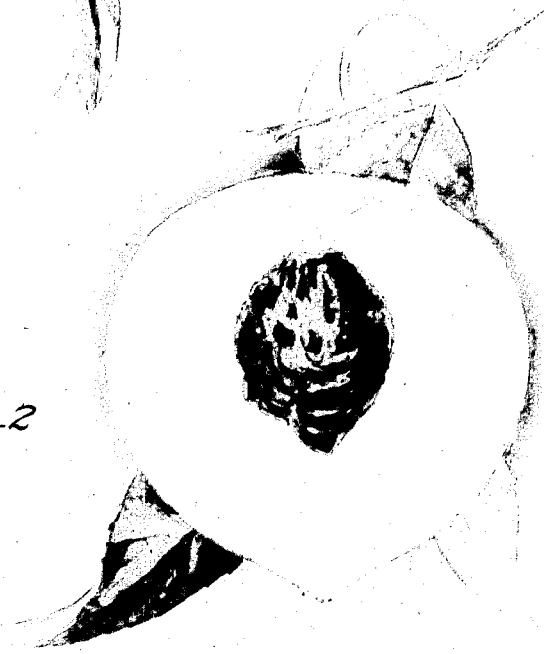
FIG. 2 is mainly a sectional elevation of one of the fruit with the stone remaining in place.

Referring now more specifically to the pomological details of this new and distinct variety of peach tree, the following is an outline description thereof; all major color plate identifications being by reference to Maerz and Paul Dictionary of Color, except where common terms of color definition are employed:

Tree:
- *Size.*—Large.
- *Vigor.*—Vigorous.
- *Growth.*—Spreading.
- *Density.*—Dense.
- *Shape.*—Vase shaped.
- *Hardiness.*—Hardy.
- *Production.*—Very productive.
- *Bearing.*—Regular bearer.

Trunk:
- *Size.*—Stocky.
- *Surface.*—Medium to rather smooth.

Branches:
- *Size.*—Medium.
- *Surface.*—Medium.
- *Color.*—Brown.
- *Lenticels.*—Number—medium. Size—medium.

Leaves:
- *Size.*—Medium. Average length—6⅖". Average width—1⅜".
- *Form.*—Lanceolate; gradually taper to point.
- *Thickness.*—Medium.
- *Texture.*—Smooth.
- *Margin.*—Finely serrate.
- *Petiole.*—Medium length; medium thickness.
- *Glands.*—Average number—two to seven. Alternate; medium size; reniform; red; positioned on petiole and blade.
- *Stipules.*—None.
- *Color.*—Top side—medium green (23–L–5). Under side—lighter green (21–K–5).

Flower Buds:
- *Hardiness.*—Hardy.
- *Size.*—Medium.
- *Length.*—Short.
- *Form.*—Plump.

Flowers:
- *Blooming period.*—Average date of first bloom—March 3rd. Average date of full bloom—March 10th. Early as compared with other varieties.
- *Size.*—Medium.
- *Color.*—Rose pink.

Fruit:
- *Maturity when described.*—Eating ripe—August 8, 1959.
- *Date of first picking.*—July 27, 1959.
- *Date of last picking.*—August 15, 1959.
- *Comparative dates of picking, eating ripe.*—Fruit of present variety—August 3–5, 1961. Fruit of the Elberta—July 30–August 1, 1961. Fruit of the Rio Oso Gem—August 7–9, 1961. All growing in the same locality in Fresno County, California, and under like conditions of soil and climate.
- *Size.*—Large. Average diameter axially—3½". Average transversely in suture plane—3".
- *Form.*—Uniform; globose-conical; slightly compressed toward suture.
- *Suture.*—Shallow, becoming deeper near base.
- *Ventral surface.*—Rounded slightly.
- *Cavity.*—Circular, with suture showing on one side. Average depth—⅜"–½". Average breadth—1".
- *Base.*—Rounded.
- *Apex.*—Short.
- *Pistil point.*—Short; pointed.

Skin:
- *Thickness.*—Medium.
- *Texture.*—Medium.
- *Tenacity.*—Tenacious to flesh.
- *Tendency to crack.*—None.
- *Down.*—Moderate; medium length.
- *Color.*—Yellow (10–J–6) to (10–G–11) partially blushed with red (6–K–6).

Flesh:
- *Amygdalin.*—Scant.
- *Juice.*—Moderate.
- *Texture.*—Firm; meaty.
- *Fibers.*—Few; fine.
- *Ripens.*—Even.
- *Flavor.*—Slightly acid.
- *Aroma.*—Distinct.
- *Eating quality.*—Good.
- *Color.*—Yellow (9–L–5) to (9–J–7), streaked with red (2–L–8) to (2–K–7) near stone. Surface of pit cavity red with yellow showing from flesh.

Stone:
- *Type.*—Free; parts from flesh smoothly; retains short fiber-like threads along ridges near base.

*Size.*—Medium. Average length—1⅘″. Average breadth—1⅕″. Average thickness—⅘″.
*Form.*—Oval.
*Base.*—Straight.
*Hilum.*—Oval.
*Apex.*—Broadly acute.
*Sides.*—Equal.
*Surface.*—Regularly furrowed toward ventral edge; slightly furrowed throughout; pitted toward base.
*Ridges.*—Rounded, but sharper toward apex.
*Pits.*—Elongated.
*Ventral edge.*—Medium thickness.
*Dorsal edge.*—Shallow groove toward base to center.
*Tendency to split.*—Very slight.
*Color.*—Brown (8–L–7).

Use: Market; dessert; shipping; canning; freezing.
Keeping quality: Good.
Shipping quality: Good.

The tree and its fruit herein described may vary in slight detail due to climatic and soil conditions under which the variety may be grown; the present description being of the variety as grown near Kingsburg, California.

The following is claimed:

A new and distinct variety of peach tree, as illustrated and described, which is hardy, vigorous and sturdy, and which tree is a regular and very productive bearer of large, good flavored freestone fruit, having yellow flesh streaked with red next to the stone and yellow skin partially blushed with red; said variety being characterized, as to novelty, by a trunk and branches which are husky and sturdy, the closest resemblance to the tree being the Rio Oso Gem; by firm fleshed fruit which highly colors and hangs well on the tree eight to twelve days before harvest, the fruit coloring before the Elberta but harvests later, and the flesh remaining firm from harvest to market; by fruit comparable in size to the Hale but more resembling the Rio Oso Gem in shape and firmness; and by fruit which is of a good commercial quality for market, dessert, shipping, canning and freezing use, the latter by reason of slow oxidization of the flesh when exposed to atmosphere.

No references cited.